(12) United States Patent
Saffari

(10) Patent No.: US 12,257,355 B2
(45) Date of Patent: Mar. 25, 2025

(54) MULTIUSE UVC STERILIZATION LIGHT, HOUSING, MOUNTS, AND ACCESSORIES

(71) Applicant: Dynotron, Inc., Salt Lake City, UT (US)

(72) Inventor: James Saffari, Salt Lake City, UT (US)

(73) Assignee: Dynotron, Inc, Salt Lake City, UT (US)

( * ) Notice: Subject to any disclaimer, the term of this patent is extended or adjusted under 35 U.S.C. 154(b) by 386 days.

(21) Appl. No.: 17/811,068

(22) Filed: Jul. 6, 2022

(65) Prior Publication Data
US 2023/0241263 A1  Aug. 3, 2023

Related U.S. Application Data

(63) Continuation-in-part of application No. 29/825,319, filed on Jan. 31, 2022, now Pat. No. Des. 1,050,561.

(51) Int. Cl.
*A61L 2/10* (2006.01)
*A61L 9/20* (2006.01)

(52) U.S. Cl.
CPC ........ *A61L 2/10* (2013.01); *A61L 9/20* (2013.01); *A61L 2202/11* (2013.01); *A61L 2202/16* (2013.01); *A61L 2209/16* (2013.01)

(58) Field of Classification Search
CPC .......... A61L 2/10; A61L 9/20; A61L 2202/11; A61L 2202/16; A61L 2209/16; A61L 2209/111; A61L 2209/15; A61L 2202/14; A61L 2202/25

See application file for complete search history.

(56) References Cited

U.S. PATENT DOCUMENTS

| | | | |
|---|---|---|---|
| 4,522,055 A * | 6/1985 | Berger | B21D 7/02 81/487 |
| 11,020,502 B1 * | 6/2021 | Medendorp, Jr. | A61L 9/20 |
| 2013/0270002 A1 * | 10/2013 | Fawcett | H01R 11/01 174/84 S |
| 2015/0244075 A1 * | 8/2015 | Platt | H01Q 1/38 343/792 |
| 2018/0055960 A1 * | 3/2018 | Reiber | A61L 2/10 |
| 2020/0188543 A1 * | 6/2020 | Etter | A61L 2/26 |
| 2022/0226522 A1 * | 7/2022 | Kurz | A61L 2/26 |

FOREIGN PATENT DOCUMENTS

| | | | | |
|---|---|---|---|---|
| CN | 201052279 Y | * | 4/2008 | |
| KR | 2003095713 A | * | 12/2003 | |
| WO | WO-9913922 A1 | * | 3/1999 | ...... A61L 2/10 |

* cited by examiner

*Primary Examiner* — David E Smith
*Assistant Examiner* — Christopher J Gassen
(74) *Attorney, Agent, or Firm* — PCFB, LLC; Justin K. Flanagan

(57) ABSTRACT

An ultraviolet sterilization system can be mounted to an air duct to sterilize the air therein and then selectively removed and used in a handheld portable mode that allows a user to sterilize a target surface. The ultraviolet sterilization system may include a housing, a heatsink element, an array of ultraviolet light-emitting diodes (LEDs) housed within the housing to generate a directional beam of ultraviolet radiation, and an electronic driver housed within the housing to drive the ultraviolet LEDs. One or more power interfaces allow for operation in an AC mode plugged into a power receptacle or in a DC mode plugged into a portable power source.

19 Claims, 16 Drawing Sheets

MULTIUSE UVC STERILIZATION LIGHT, HOUSING, MOUNTS, AND ACCESSORIES

RELATED APPLICATIONS

This application is a continuation-in-part of U.S. Design patent application No. 29/825,319, filed on Jan. 31, 2022, titled "UVC Sterilization Light Housing," which application is hereby incorporated by reference in its entirety.

TECHNICAL FIELD

This disclosure generally relates to portable and multiuse light housing. In particular, this application relates to ultraviolet sterilization lights, including ultraviolet C ("UVC") lights.

DETAILED DESCRIPTION

Figure 1:
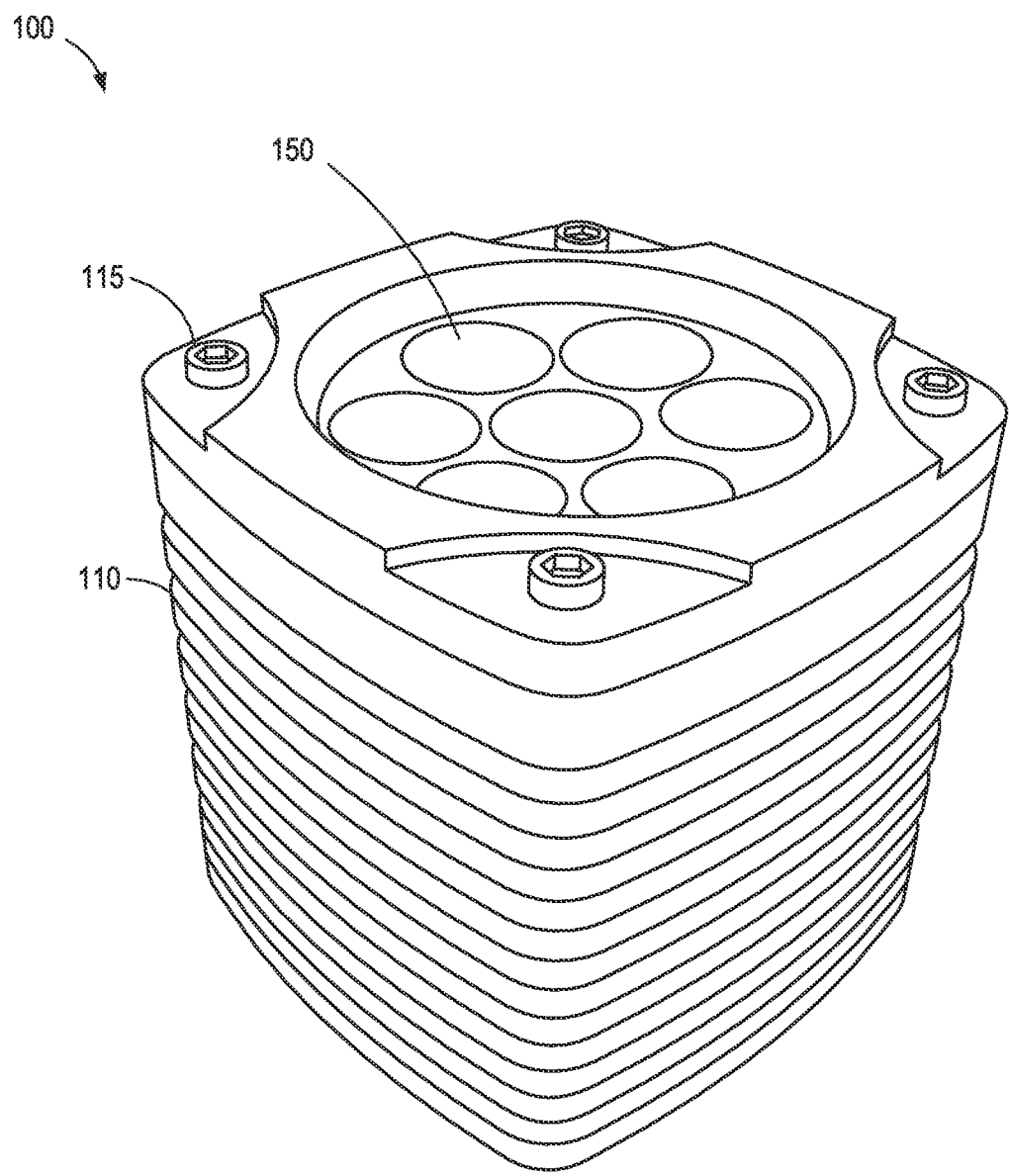
FIG. 1 illustrates an example of a UVC light, according to one embodiment.

The features, structures, and operations associated with one embodiment may be applicable to or combined with the features, structures, or operations described in conjunction with another embodiment. In some instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once.

According to various embodiments, an ultraviolet sterilization system includes an ultraviolet light assembly that can be selectively mounted, secured, and released from various locations. For example, the ultraviolet light assembly may be selectively connected to and disconnected from the ductwork of a heating, ventilation, and air conditioning (HVAC) system. The ultraviolet light assembly may be used in a handheld portable configuration for sterilization of surfaces. The ultraviolet light assembly may be selectively disconnected from and connected to a desktop mount for sterilizing objects placed under a fixed (or adjustable) zone of illumination. In some embodiments, one or more ultraviolet light assemblies may be connected to a portable cart or stand that can automatically (e.g., self-driving, autonomously, or randomly) or manually be moved through a facility to sterilize floors, walls, ceilings, air, and objects within a room, or other surfaces. On other examples, the UVC lights may be used to clean tables in a restaurant, a school facility, a hospital, and/or other facilities.

In various embodiments, the ultraviolet light assembly includes a housing, a heatsink element (that may be connected to or form part of the housing), an array of ultraviolet light-emitting diodes (LEDs), a driver to control the operation of the ultraviolet LEDs, and one or more power interfaces to receive power from an external source.

In some embodiments, a complete system may further include specific mounting interfaces that are configured to selectively maintain the ultraviolet light assembly in various fixed or portable configurations. For example, the system may include a duct mounting interface that can be secured proximate to a hole or opening in an air duct (e.g., of an HVAC system, sterilization system, fan assembly, blower assembly, intake, outflow, etc.). The mounting interface may be configured for permanent or temporary installation on the air duct or other surfaces, such as a desktop mount, a ceiling mount, a portable cart mount, a handheld wand or handle, etc. The mounting interface is further configured to selectively retain and disengage the ultraviolet light assembly. For example, the mounting interface may include tabs, screws, friction interfaces, snap interfaces, twist-lock interfaces, etc. that interact with corresponding interfaces on the ultraviolet light assembly.

In some embodiments, the complete kit or system may include one or more power supplies. For example, a first power supply may include a converter to convert alternating current (AC) power from a wall receptacle to direct current (DC) power for delivery via a plug interface or wireless power interface on the ultraviolet light assembly. A second power supply may comprise a DC power source, such as a battery, capacitor, or combination thereof, to deliver DC power directly to the same plug or wireless power interface.

In other embodiments, the ultraviolet light assembly includes an integrated AC to DC converter. The ultraviolet light assembly may automatically detect if incoming power is AC or DC and covert the power as necessary for the operation of the ultraviolet light assembly. Thus, in one example, the ultraviolet light assembly can be selectively mounted in a semi-permanent configuration to an air duct to sterilize the air passing therethrough. During this operational state, the ultraviolet light assembly may be mounted to the mounting interface and receive power from the first power supply plugged into an AC power wall receptacle in a room of a building. A user may want to use the ultraviolet light assembly to sterilize a surface in another room of the building. Accordingly, the user may selectively disengage the ultraviolet light assembly from the mounting interface on the air duct and disconnect the first power supply. The user may then connect a battery or other portable power supply to the ultraviolet light assembly and use the ultraviolet light assembly in a handheld operational state to sterilize a surface within a region illuminated by a directed beam of ultraviolet radiation generated by the ultraviolet light assembly. The user may move the ultraviolet light assembly around as needed to sterilize a larger surface and/or other objects.

According to some embodiments, the ultraviolet light assembly may include a user-adjustable focusing lens, reflector, or shroud to focus or change the spot size of the directional beam of ultraviolet radiation. In some embodiments, the ultraviolet LEDs are configured to generate ultraviolet C (UVC) optical radiation at a wavelength or band of wavelengths selected for specific sterilization properties. Similarly, the strength of the ultraviolet radiation generated, and the corresponding spot size of the focus or directional beam of ultraviolet radiation may be selected for a particular kill time of specific types of germs, bacteria, viruses, etc. In some instances, the ultraviolet light assembly may be used as a cure light or for other industrial and commercial purposes.

According to various embodiments, the ultraviolet light assembly may include an elongated handle that can be selectively bent and repositioned by a user to maintain a target shape during portable use and/or while installed on an air duct, vacuum, portable cart, and/or other appliances. The elongated handle may be removable in some embodiments. Additionally, in some embodiments, the elongated handle may include an integrated power cord and/or integrated batteries or another power source. In some embodiments, the ultraviolet light assembly may include integrated batteries (e.g., rechargeable batteries), capacitors, single-use disposable batteries, or the like. In some instances, integrated batteries of the ultraviolet light assembly are charged while it is mounted within a mounting interface of an air duct so that it is ready to be removed and immediately used in a handheld operational mode or on a portable device (cart, vehicle, etc.).

As previously described, in some embodiments, the housing of the ultraviolet light assembly comprises or is formed in part by the heatsink. In some instances, fins of the heatsink itself may interface with the mounting assemblies to selectively retain the ultraviolet light assembly in the various mounted operational modes.

In some instances, the intensity of the ultraviolet radiation may be varied or changed based on the mounting or operational state. For example, the ultraviolet light assembly may include a driver or other controller that automatically limits the total power or intensity of the ultraviolet radiation during operation in a handheld operational mode (e.g., due to health or safety risks). The driver or other controller may detect that the ultraviolet light assembly is mounted to an air duct and increase the power and/or intensity of the ultraviolet radiation to increase the kill rate or sanitization effectiveness and/or in response to the availability of fixed power vs portable power.

In some embodiments, the ultraviolet light assembly may be selectively mounted to a wall mounting interface configured to be permanently secured to a wall and to selectively secure and release the ultraviolet light assembly from a wall-mounted position. In another embodiment, the ultraviolet light assembly may be selectively mounted to a desktop mounting stand configured to be placed on a planar surface and to selectively secure and release the ultraviolet light assembly from a desktop mounted position. In another embodiment, the system or kit may include a portable large surface cleaning mount configured to selectively secure and release multiple ultraviolet light assemblies for mobile sterilization of large surfaces. The portable large surface cleaning mount may have an integrated power supply and power cords to connect multiple ultraviolet light assemblies. In some embodiments, the ultraviolet light assemblies are configured with power interfaces that allow for daisy-chaining of the ultraviolet light assemblies on the portable large surface cleaning mount to reduce wire clutter.

Embodiments may be best understood by reference to the drawing(s), wherein like parts are designated by like numerals throughout. It will be readily understood that the components of the present disclosure, as generally described and illustrated in the drawing(s) herein, could be arranged and designed in a wide variety of different configurations. Thus, the following detailed description of the embodiments of the systems, methods, and apparatuses is not intended to limit the scope of the disclosure but is merely representative of possible embodiments of the disclosure. In some cases, well-known structures, materials, or operations are not shown or described in detail.

FIG. 1 illustrates an example of an ultraviolet C (UVC) light 100, according to one embodiment. As illustrated, the UVC light 100 includes multiple UVC light-emitting diodes (LEDs) 150 within a housing 110 that includes heatsink fins. The housing may include, in some embodiments, a glass, acrylic, sapphire, polycarbonate, or another transparent cover over the LEDs 150 as part of the upper housing that is secured to the heatsink portion of the housing 110 via one or more fasteners 115.

Figure 2A:
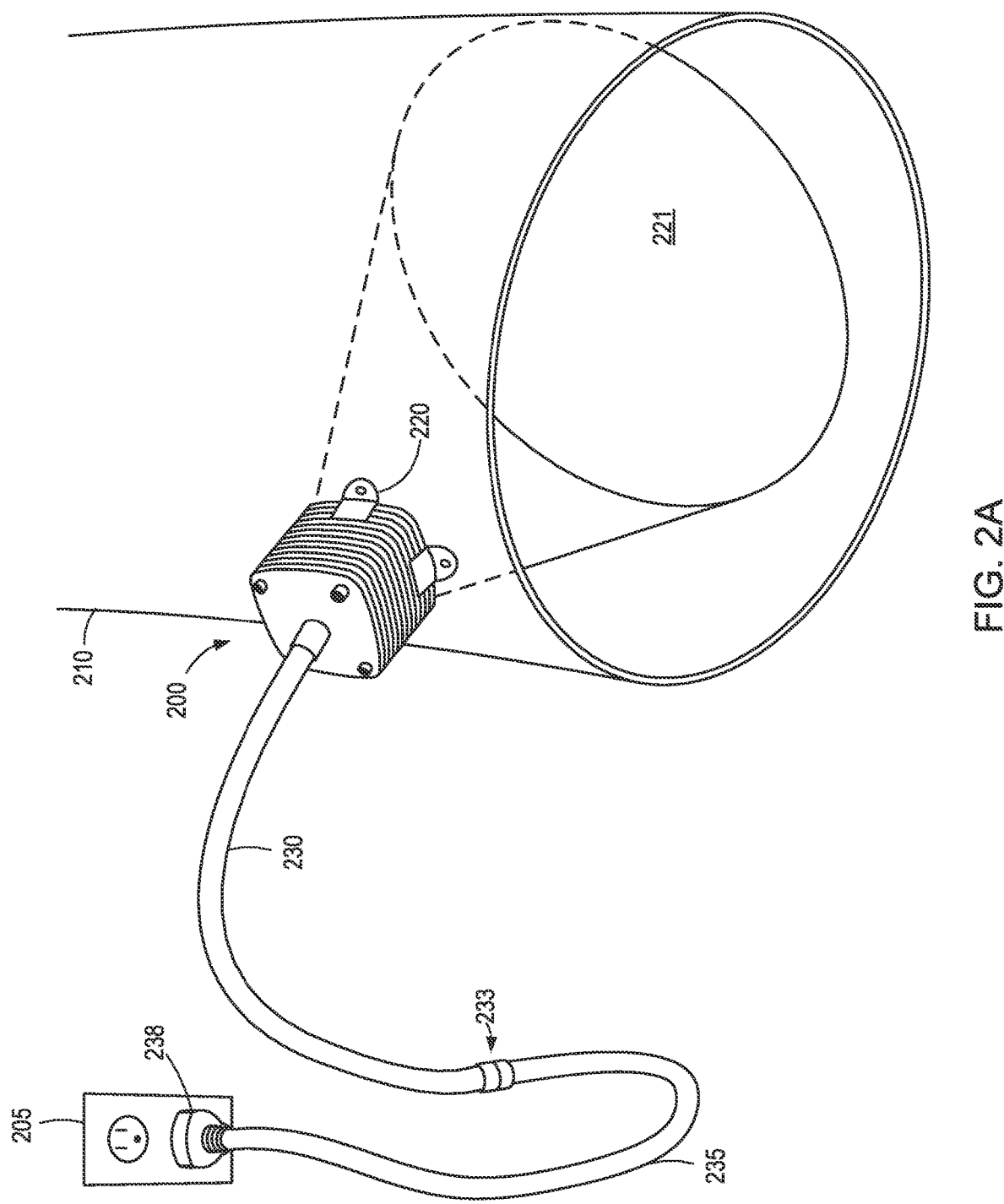
FIG. 2A illustrates a UVC light plugged in and mounted to a duct of a heating, ventilation, and air conditioning (HVAC) system, according to one embodiment.

FIG. 2A illustrates a UVC light 200 plugged in and mounted to a duct 210 of a heating, ventilation, and air conditioning (HVAC) system, according to one embodiment. As illustrated, the UVC light 200 may be temporarily, selectively, and/or releasably secured to the duct 210 via a duct mounting interface 220. In the illustrated embodiment, the duct mounting interface 220 includes four mounting tabs that are secured to the duct (e.g., via screws, rivets, an adhesive, or another fastener). The four mounting tabs may, in some embodiments, be part of a single mounting interface. In the illustrated embodiment, the four mounting tabs of the duct mounting interface 220 provide a friction fit against fins of a heatsink of the housing of the UVC light 200 that selectively retain the UVC light 200 secured to the duct 210.

As illustrated, in a duct-mounted position and operational mode, the UVC light 200 illuminates a large region 221 within the duct 210 that is sterilized by UVC radiation, including particles and other objects (e.g., viruses, bacteria, mold, fungus, etc.) within air passing through the duct 210. In some embodiments, the UVC light 200 may detect the mounting and/or operational configuration and adjust (e.g., increase or decrease) a focus, intensity, power, or another characteristic of the emitted UVC radiation emitted by the UVC light 200. In some embodiments, the emitted UVC radiation may be constantly emitted and in other embodiments, it may be pulse-width modulated. In some embodiments, a controller may vary the power driving UVC LEDs of the UVC light 200 based on a measured temperature and/or airflow within the duct. For example, the controller may decrease the power driving the UVC LEDs of the UVC light 200 when a temperature associated with the UVC LEDs or the heatsink on the housing of the UVC light 200 exceeds a thermal threshold to avoid damage to the UVC light 200. In some embodiments, the UVC light 200 may include a sensor to detect airflow within the duct 210. When there is no airflow, a controller of the UVC light 200 reduces the power output and/or turns off the LEDs completely to preserve power and/or the life of the UVC LEDs.

In some embodiments, the controller may report the total "on time" of the UVC LEDs. In such an embodiment, instead of requiring replacement LEDs after a certain number of hours, months, years, etc., the controller may provide an accurate estimate of the amount of life left based on the actual "on time" when the air was actually flowing within the duct 210.

As illustrated, the UVC light 200 may include an integrated or detachable cord 230 that can be selectively attached and detached from a power supply cord 235 via a cord coupling 233. In the illustrated configuration in which the UVC light 200 is mounted to the duct 210 in a fixed, duct sterilization operational mode, the UVC light 200 may be powered by power from a power receptacle 205 in a wall. The power receptacle 205 may provide alternating current (AC) that is converted to direct current (DC) by an external AC to DC converter 238. In other embodiments, the UVC light 200 may include an internal and integrated AC to DC (AC/DC) converter that automatically detects whether supplied power is AC or DC and convert as necessary for internal operation and to drive the LEDs of the UVC light 200.

Figure 2B:
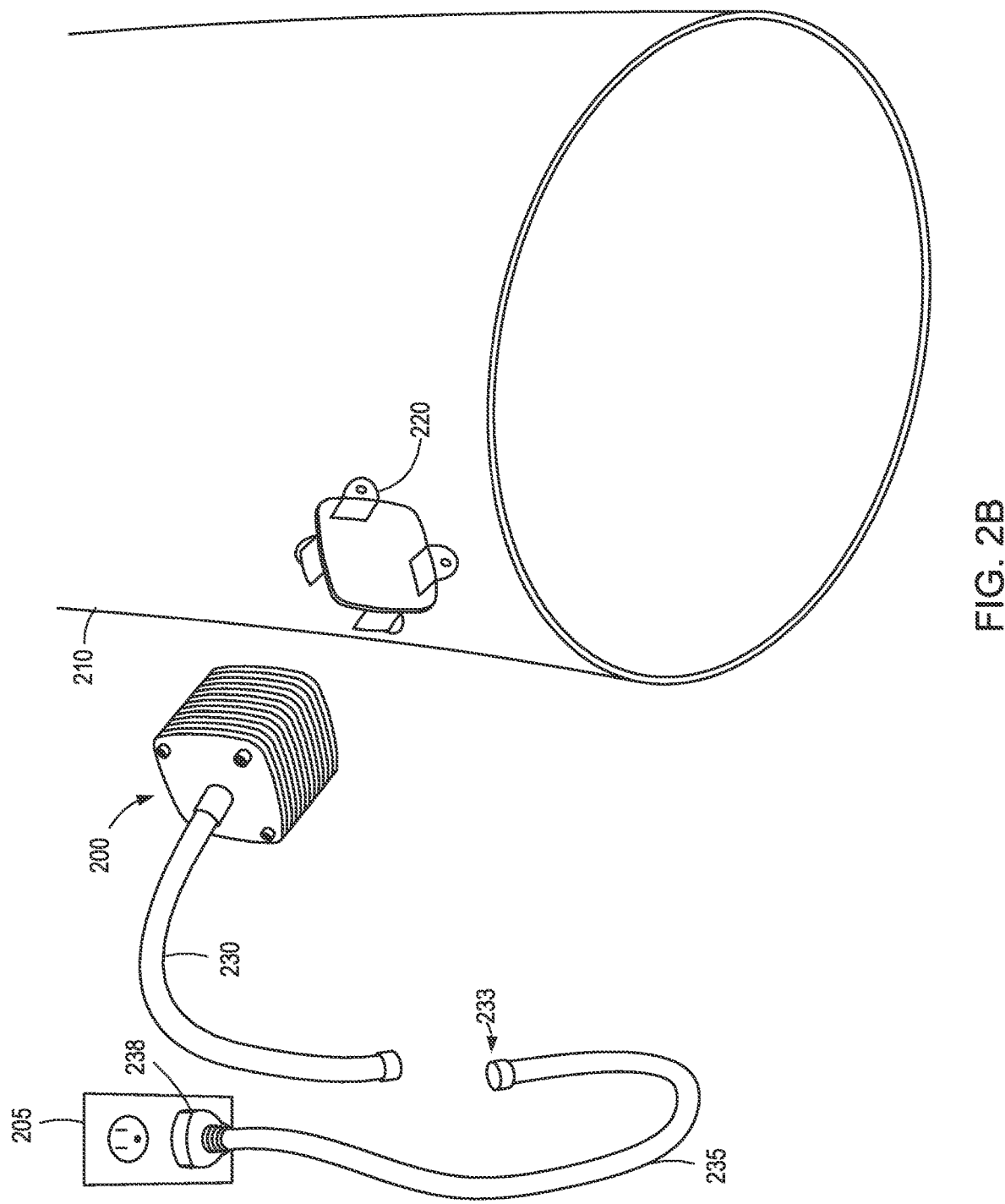
FIG. 2B illustrates the UVC light of FIG. 2A unplugged and detached from a mount on the duct of the HVAC system for portable sterilization use, according to one embodiment.

FIG. 2B illustrates the UVC light 200 of FIG. 1A unplugged and selectively detached from the duct mounting interface 220 on the duct 210 of the HVAC system for portable sterilization use, according to one embodiment. As illustrated, the cord coupling 233 allows the detachable cord 230 to be detached from the power supply cord 235 and associated AC/DC converter 238. In some embodiments, the duct mounting interface 220 includes a plug that can be selectively placed over the hole in the duct 210 while the UVC light 200 is being used elsewhere. In other embodiments, the duct mounting interface 220 includes a flap that is external or internal to the duct that automatically covers the hole in the duct 210 when the UVC light 200 is removed from the duct 210.

Figure 2C:
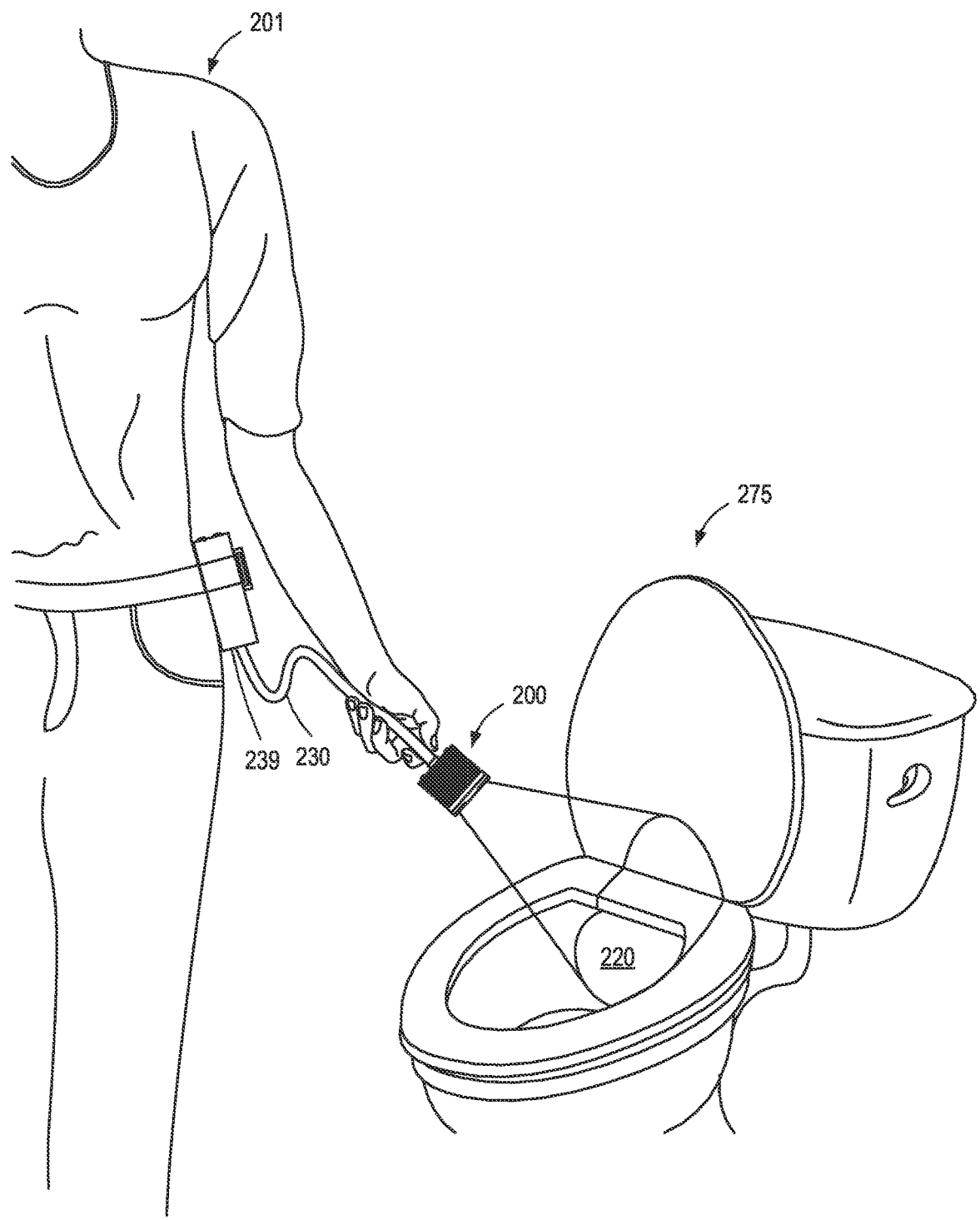
FIG. 2C illustrates the UVC light of FIG. 2A plugged into a portable power source during portable sterilization use, according to one embodiment.

FIG. 2C illustrates the UVC light 200 of FIG. 1A plugged into a portable power source 239 during portable sterilization use, according to one embodiment. As illustrated, an operator or user 201 is able to hold the cord 230 like a handle while using the UVC light 200 to illuminate a surface of a toilet 275 with UVC within a region 220. In some embodiments, the cord 230 may include a ridged texture that provides for some flexibility and also allows for the cord to be repositioned and maintain its shape. That is, the cord 230 may double as a handle that is rigid, flexible, flexibly repositionable, includes repositionable segments, includes a ball head, or otherwise allows the UVC light 200 to be repositioned with respect to the cord 230.

In some embodiments, the UVC light 200 includes a controller that detects that the UVC light 200 is in a portable operational mode and adjusts characteristics of the UVC light 200 accordingly. For example, the controller may reduce the power or intensity of the output UVC light 200 during portable use to reduce power consumption or maintain the total output power level within a safe operating range and/or comply with regulations and laws governing UVC light output.

In one embodiment, the UVC light 200 may include a motion sensor that is used during portable operational mode to detect movement of the UVC light 200. If the UVC light 200 is held stationary, an internal timer may initiate that will turn off the UVC light 200 after a time period that is sufficient to sterilize the illuminated region. For example, the user 201 may be informed to hold the UVC light 30 centimeters from a surface for sterilization within 5 seconds. The controller may detect that the UVC light 200 is being held stationary and illuminate the region for 5 seconds before turning off to inform the user 201 that the illuminated region 200 has been sterilized. The user 201 may then move the UVC light 200 to a new position and the controller will drive the UVC light 200 for 5 seconds in the new location.

In some embodiments, the UVC light 200 may also detect the distance to the surface being sterilized. For a given intensity of UVC radiation, the controller may determine or be programmed with specific kill times for effective sterilization based on the distance the UVC light 200 is being held from the surface or object being sterilized. For example, the UVC light 200 may illuminate a region that is 10 centimeters away for only 3 seconds before turning off to alert the user 201 that the region has been sterilized. If the UVC light 200 is held 40 centimeters away from a region and held stationary, the UVC light 200 may remain on for 10 seconds. The exact amount of time and acceptable distances depends on the intensity of the UVC radiation and the focus or spot size of the emitted UVC radiation. In some embodiments, rather than turn off after an effective sterilization time period has expired, the UVC light 200 may alert the user 201 that sterilization is complete by an audible beep and/or haptic feedback.

In some embodiments, the UVC light 200 may be attached to a mounting interface for a buck or container for sanitizing the contents thereof. For example, the UVC light 200 may be mounted to a mounting interface on a gallon jug of water to sanitize the water.

Figure 3:
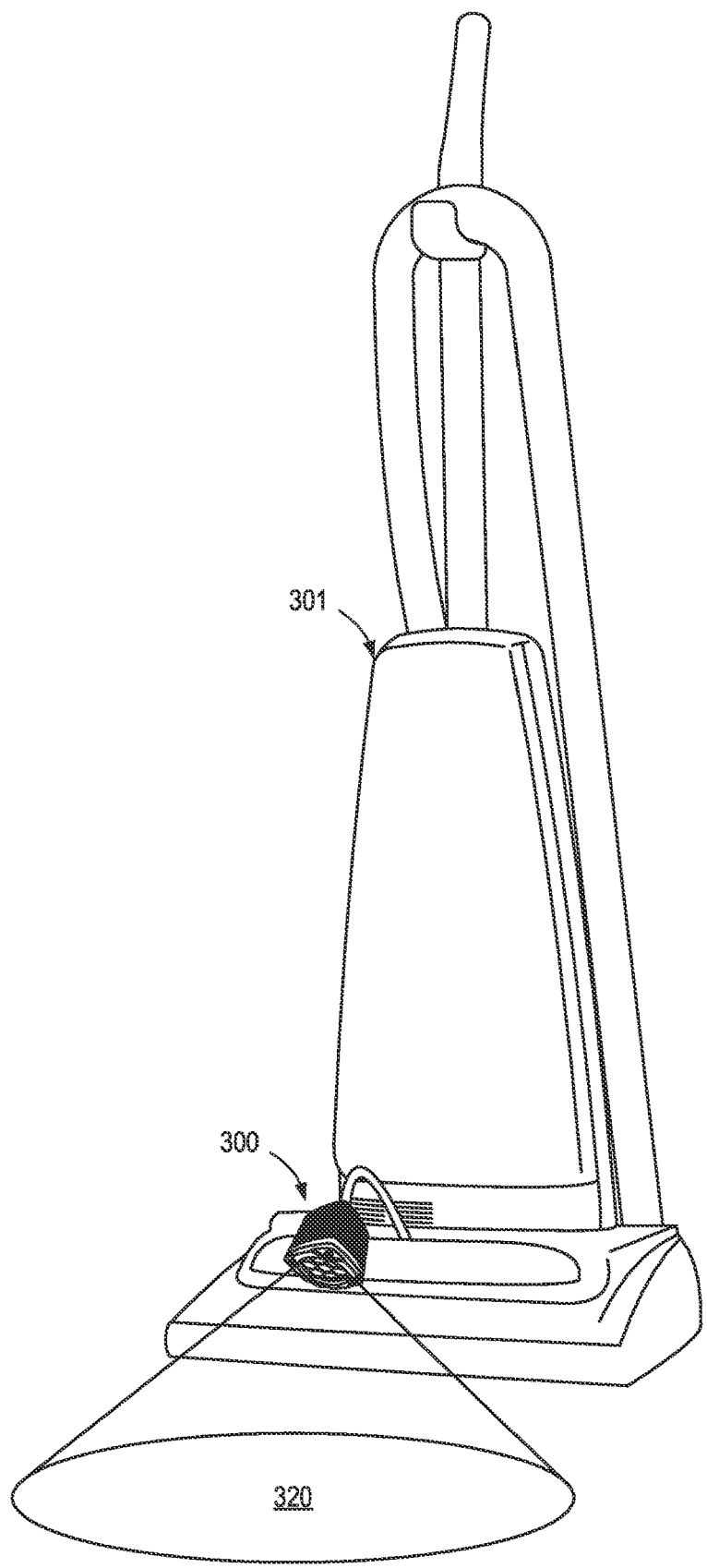
FIG. 3 illustrates a UVC light mounted to a vacuum to provide portable sterilization of a floor, according to one embodiment.

FIG. 3 illustrates a UVC light 300 mounted to a vacuum 301 to provide portable sterilization of a region 320 on a floor (e.g., carpet or a hard surface flooring), according to one embodiment. According to various embodiments, a purpose-built mounting interface may be used to secure the UVC light 300 to various objects, including the vacuum 301, and the UVC light 300 may be powered by a connected battery or other portable power supply. In other embodiments, the vacuum 301 or other appliance may be specifically designed for use with the UVC light 300 and include an integrated mounting interface and power connection to be directly connected to the UVC light 300. In such an embodiment, a user may generally leave the UVC light 300 mounted to an air duct for air purification and sterilization. The user may then selectively remove the UVC light 300 from the air duct for use with the vacuum 301 when desired.

Figure 4:
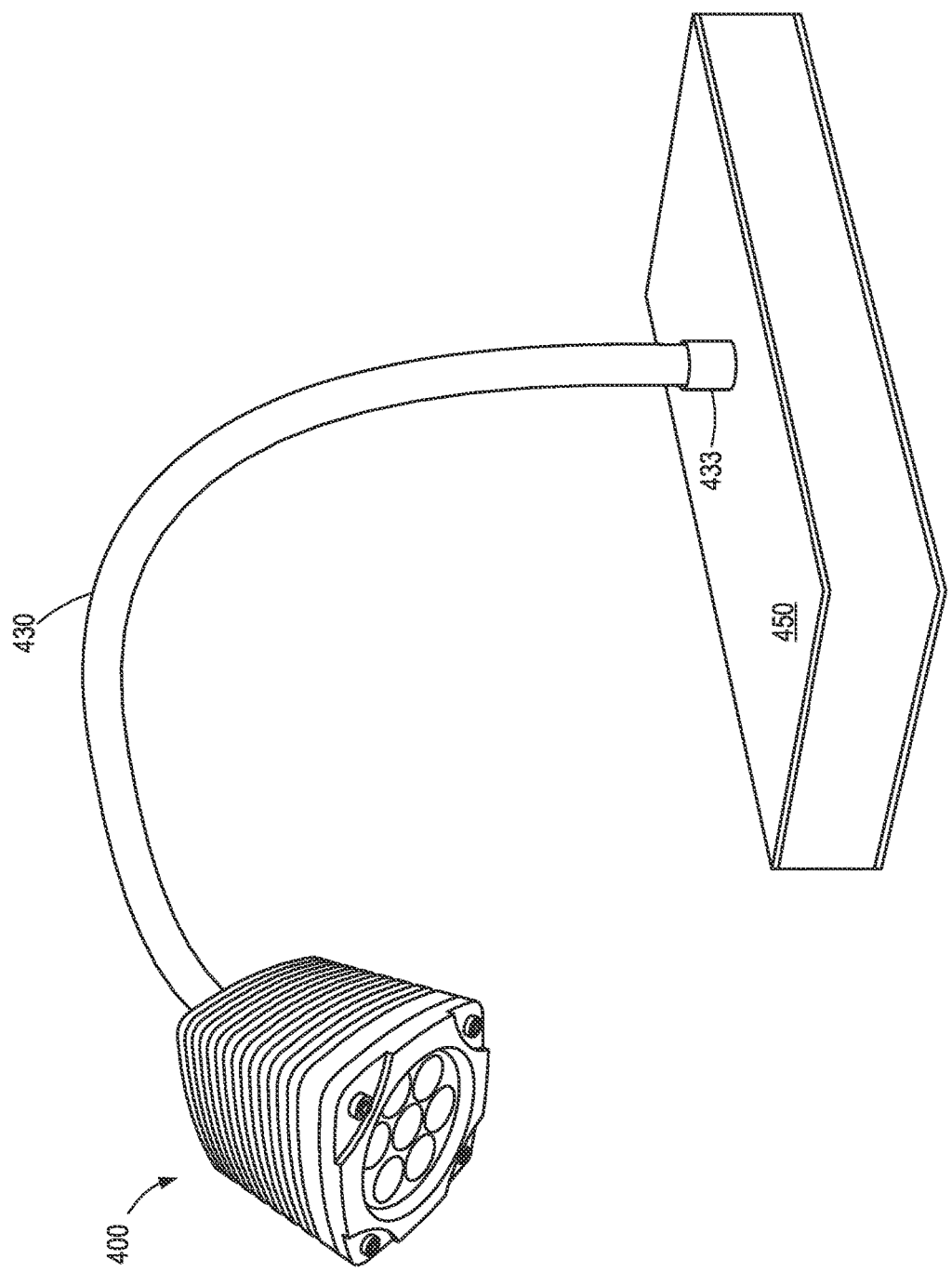
FIG. 4 illustrates a UVC light mounted on a platform for desktop and small-item sterilization, according to one embodiment.

FIG. 4 illustrates a UVC light 400 mounted on a platform 450 for desktop and small-item sterilization, according to one embodiment. In some embodiments, a rigid, semi-rigid, flexible, and/or repositionable cord 430 may be selectively disconnected from use with an air duct (e.g., cord 230 in FIG. 2) and plugged into the platform 450 using cord coupling 433. The platform 450 may include a power cord that is plugged into another power receptacle and/or an integrated power supply. A user may bend or otherwise reposition the UVC light 400 to illuminate a region on a desk or tabletop that can be used as a stationary location to sanitize objects placed therein. For example, the user may place keys, cell phones, wallets, utensils, and/or any other object within the illuminated region for sterilization.

As in other embodiments, the UVC light 400 in the desktop operational mode may remain on until the user turns it off (e.g., via a button or switch). In other embodiments, the UVC light 400 may automatically shut off after a predetermined time. In still other embodiments, the UVC light 400 may detect that it is in the desktop operational mode and turn on for a predetermined amount of time each time that it detects motion within the illuminated region. Thus, a controller of the UVC light 400 may turn on the UVC light 400 when it detects the motion of an object being placed within the irradiated region for an amount of time sufficient for sterilization. The UVC light 400 may be turned off after the sterilization is complete until it detects the motion of another object being placed within the illuminated region.

In some embodiments, the object detection sensor may be the same sensor used in the desktop operation mode used to detect the UVC light 400 being held stationary in the handheld operational mode (e.g., in FIG. 2C). In some embodiments, the user actively informs the controller of the UVC light 400 which operational mode is being used (e.g., via a switch, toggle, Bluetooth, NFC, etc.). In other embodiments, the controller of the UVC light 400 automatically determines the operational mode based on the power source, RFID tags in the mounting interface, wireless communication between the UVC light 400 and the mounting interface, or the like.

Figure 5A:
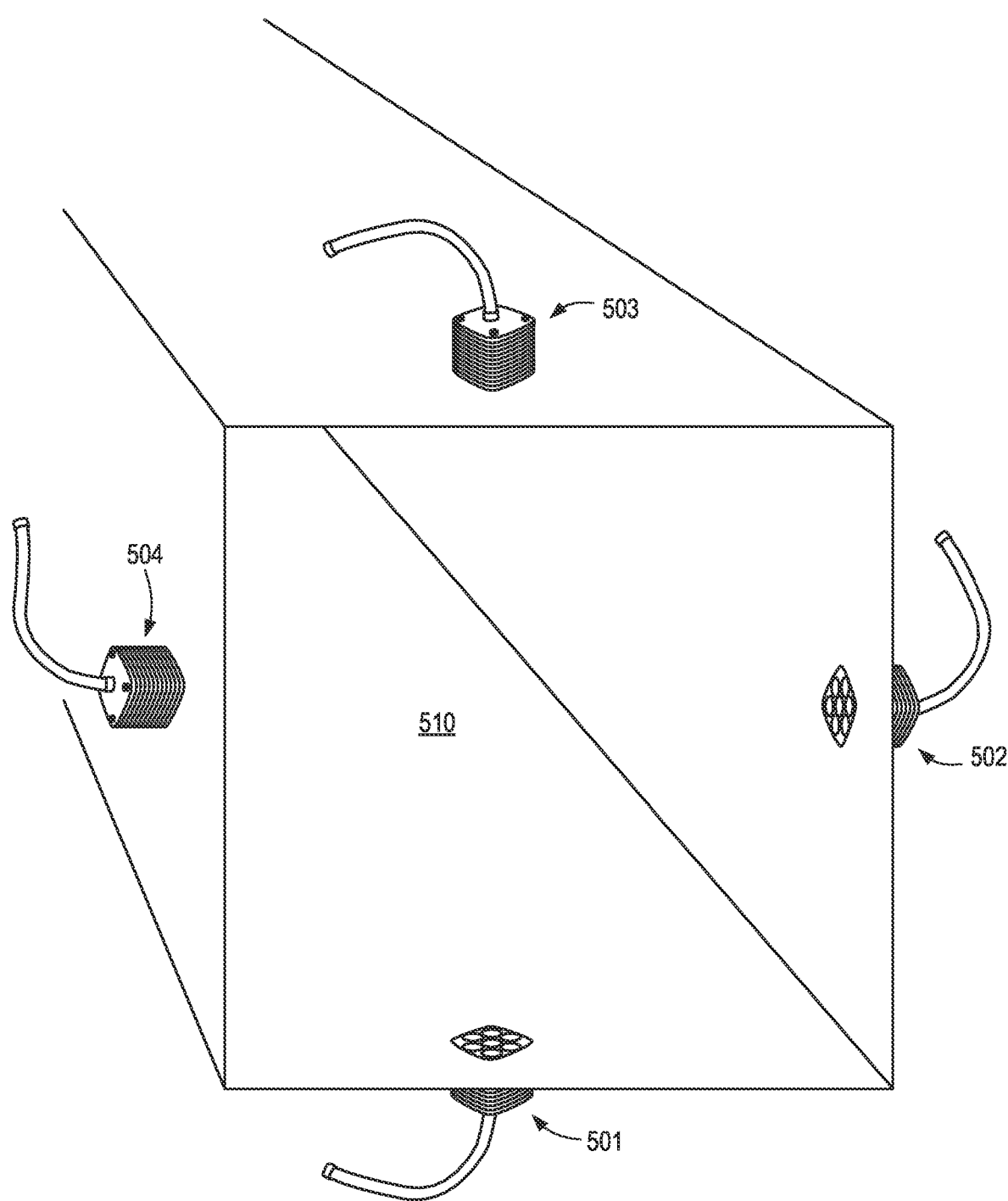
FIG. 5A illustrates four UVC lights mounted to a duct of a commercial HVAC system, according to one embodiment.

FIG. 5A illustrates four UVC lights 501, 502, 503, and 504 mounted to a duct 510 of a commercial HVAC system, according to one embodiment. As previously described, each of the four UVC lights 501, 502, 503, and 504 may be connected via a duct mounting interface that remains permanently attached to the duct 510 when the UVC lights 501, 502, 503, and 504 are removed. The UVC lights 501, 502, 503, and 504 operate to transmit UVC radiation into the duct to sterilize air therein to kill bacteria, pathogens, molds, fungi, viruses, and the like.

Figure 5B:
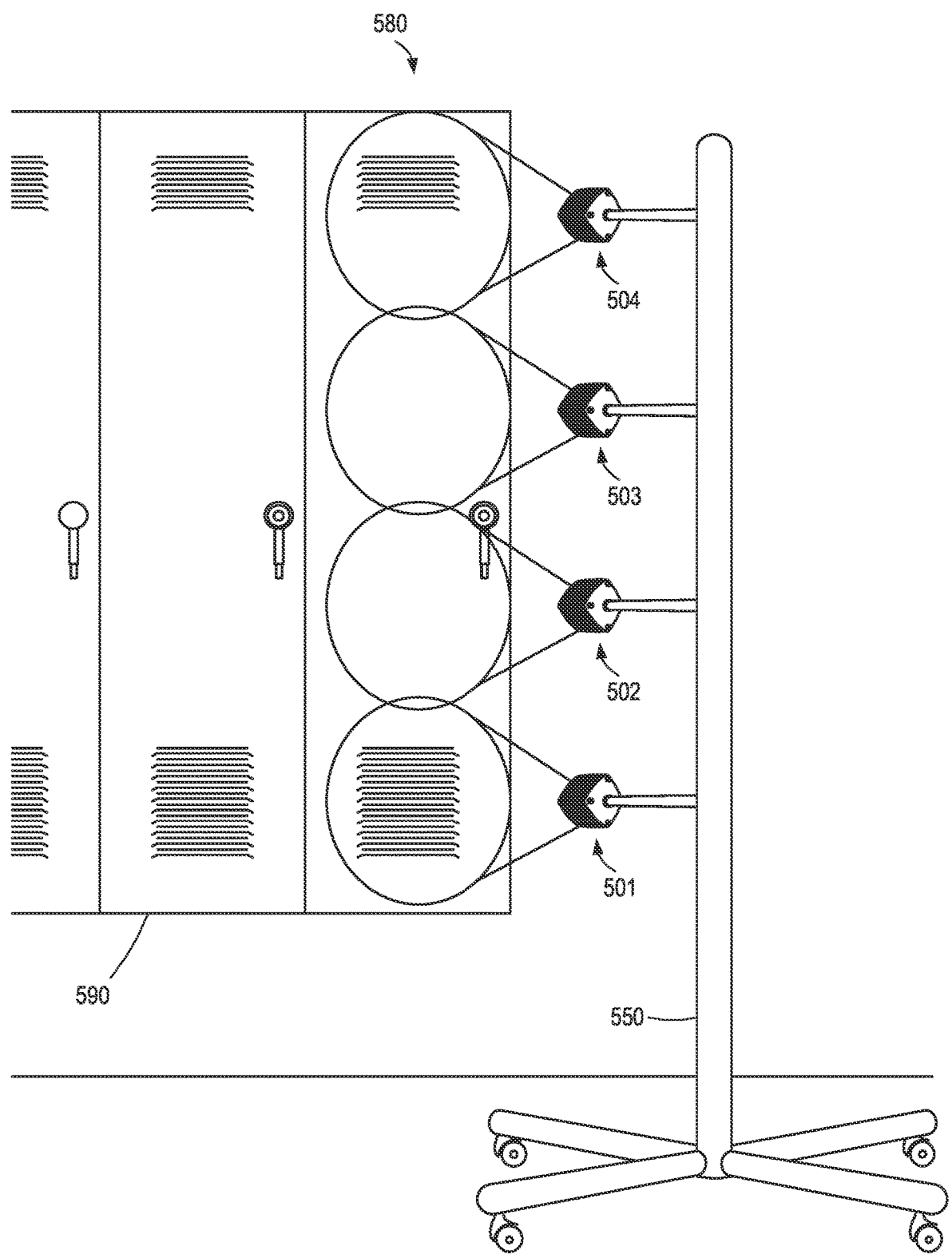
FIG. 5B illustrates the four UVC lights of FIG. 5A mounted to a mobile pole for large surface sterilization, according to one embodiment.

FIG. 5B illustrates the four UVC lights 501, 502, 503, and 504 of FIG. 5A mounted to a mobile pole 550 for large surface sterilization, according to one embodiment. In the illustrated example, the pole 550 includes wheels to be pushed down a hallway while the UVC lights 501, 502, 503, and 504 irradiate a large region 580 of a wall that includes lockers 590. In the illustrated example, the UVC lights 501, 502, 503, and 504 may be temporarily removed from the duct 510 (FIG. 5A) where they are used to sterilize the air circulating within the facility, and positioned on a portable cart 550 to sanitize surfaces of the facility.

Figure 6A:
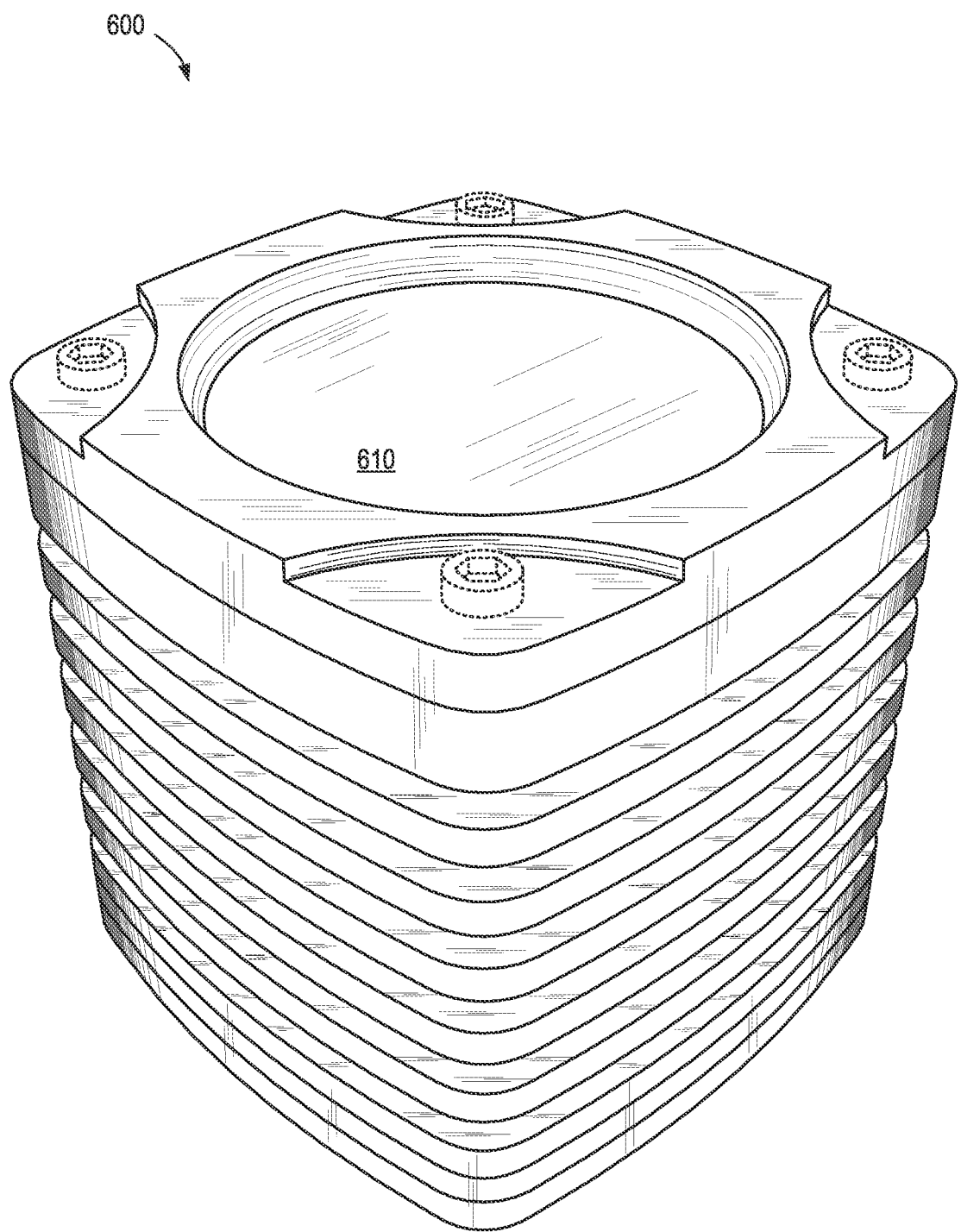
FIG. 6A is a top perspective view of a UVC light housing, according to one embodiment.

FIG. 6A is a top perspective view of a UVC light housing 600, according to one embodiment. As illustrated, the UVC light housing 600 may include a glass, acrylic, polycarbonate, sapphire, or other transparent lens or covering 610 to allow UVC radiation to escape from the UVC light housing 600. One or more lens assemblies, reflectors, shrouds, mirrors, or the like may be used to focus or direct generated UVC radiation to a spot size having a target shape and size (e.g., circular or another target shape for a given object or region to be irradiated).

Figure 6B:
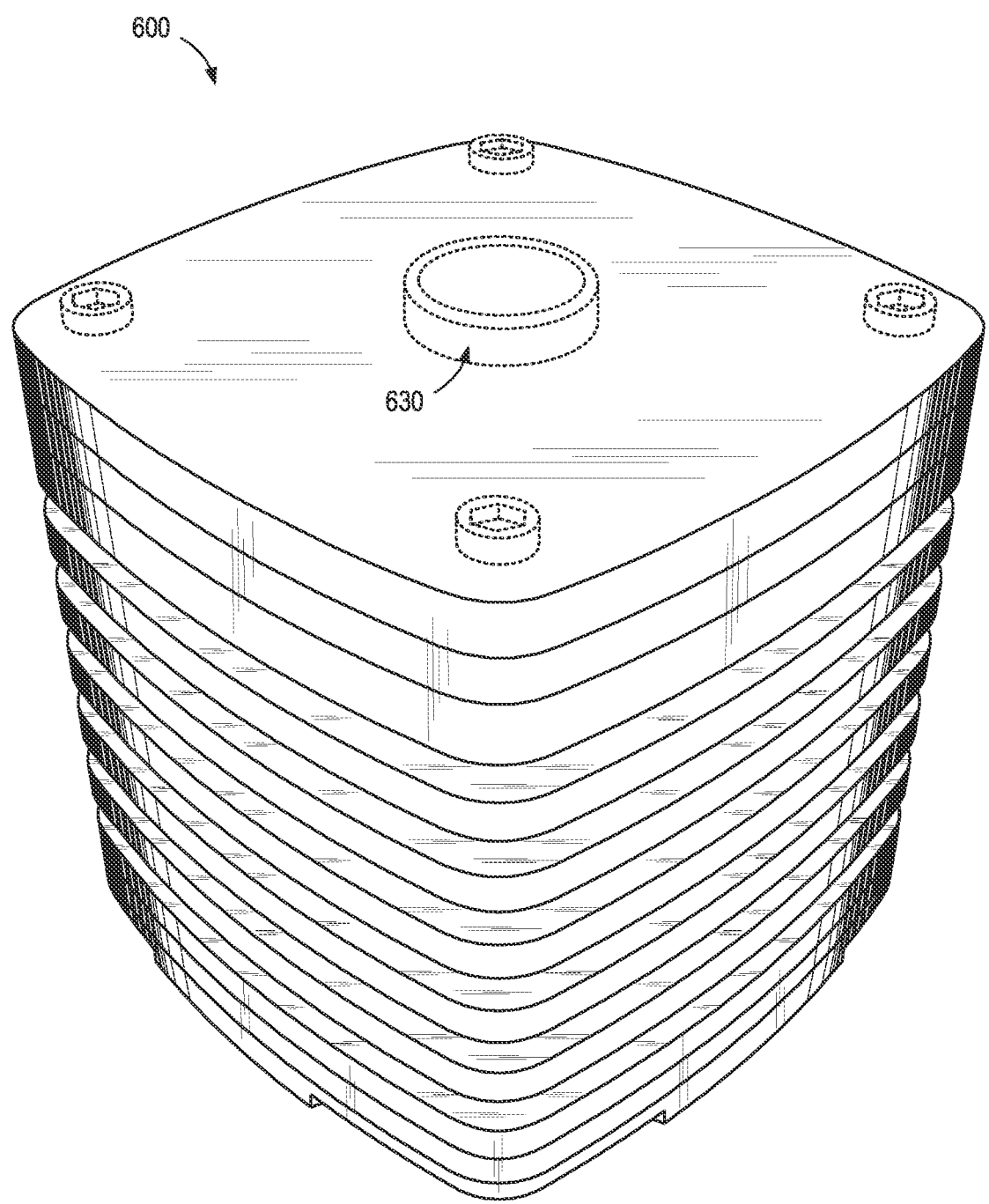
FIG. 6B is a bottom perspective view of the UVC light housing of FIG. 6A, with phantom lines depicting a central electrical cord input, according to one embodiment.

FIG. 6B is a bottom perspective view of the UVC light housing 600 of FIG. 6A, with phantom lines depicting a central electrical cord input 630, according to one embodiment. As previously described, the electrical cord input 630 may include a detachable interface for an electrical cord connection, a wireless power interface, and/or a fixed cord or handle containing a cord.

Figure 6C:
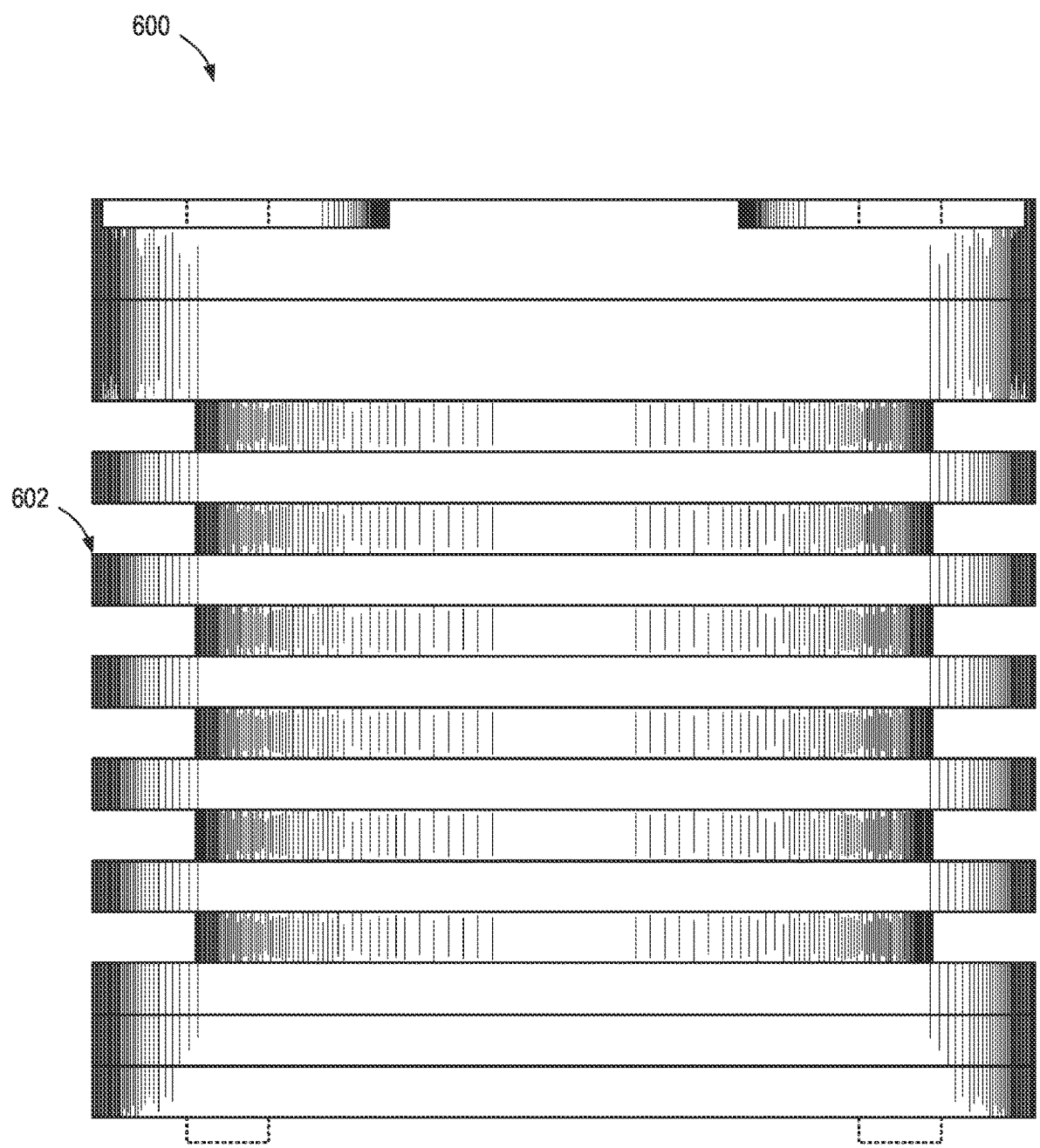
FIG. 6C is a right-side elevation view of the UVC light housing of FIG. 6A, according to one embodiment.

FIG. 6C is a right-side elevation view of the UVC light housing 600 of FIG. 6A, according to one embodiment. The right side elevation view of the UVC light housing 600 shows the alternating spacing of heatsink fins 602 that are integral with the UVC light housing 600 and operate to cool the UVC light housing 600, an internal power source, an internal AC/DC power converter, an internal LED driver, and/or UVC LEDs.

Figure 6D:
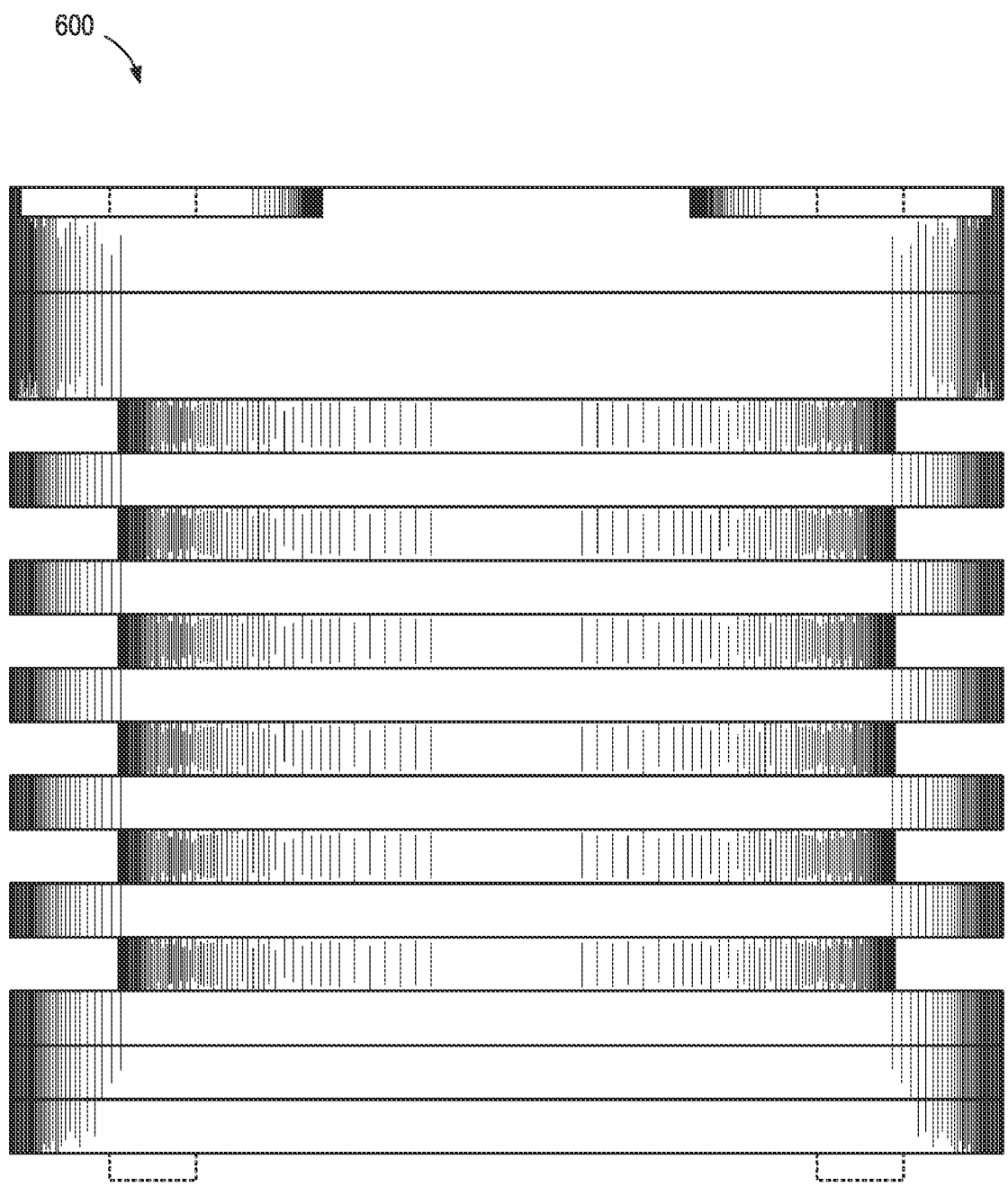
FIG. 6D is a left-side elevation view of the UVC light housing of FIG. 6A, according to one embodiment.

FIG. 6D is a left-side elevation view of the UVC light housing of FIG. 6A, according to one embodiment.

Figure 6E:
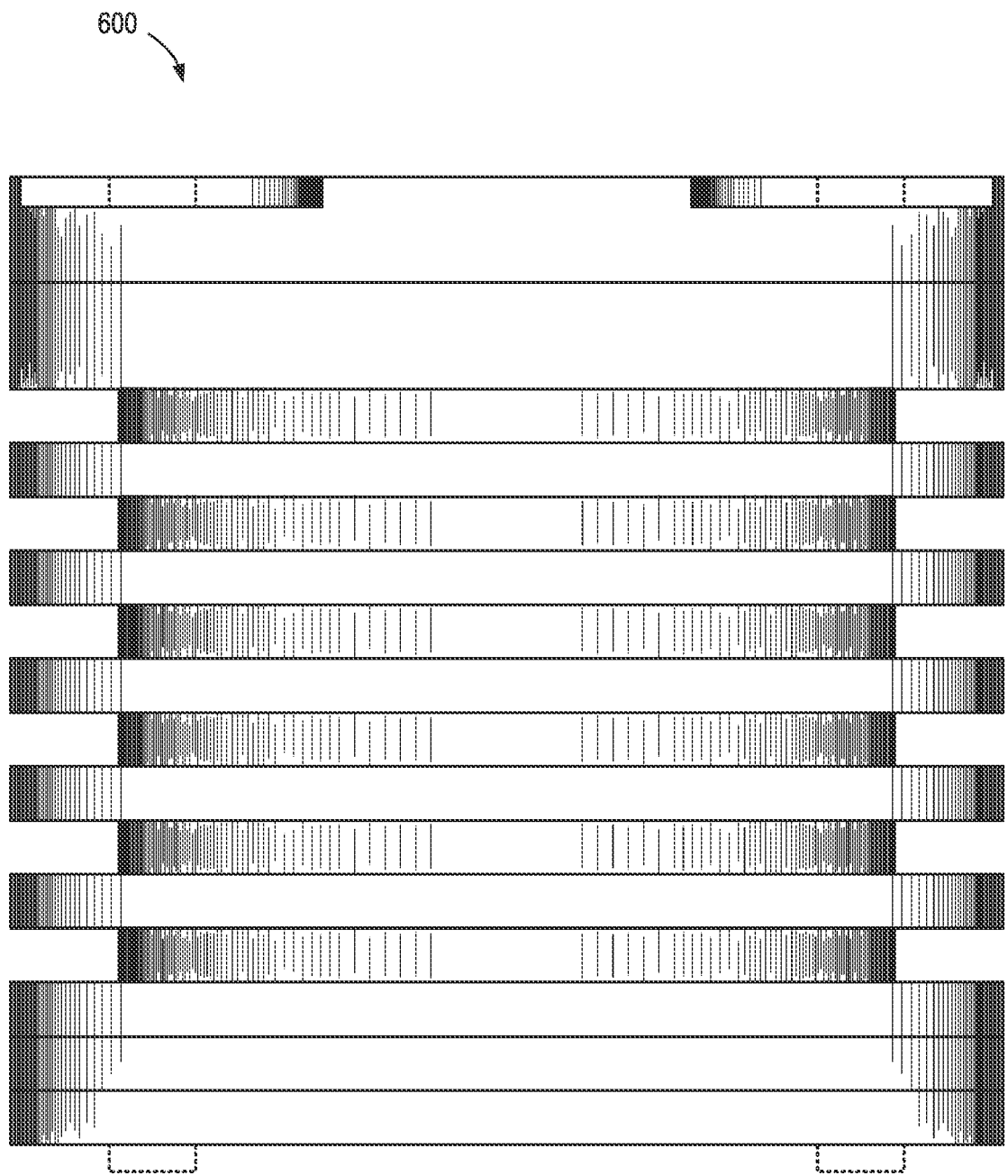
FIG. 6E is a front-side elevation view of the UVC light housing of FIG. 6A, according to one embodiment.

FIG. 6E is a front-side elevation view of the UVC light housing of FIG. 6A, according to one embodiment.

Figure 6F:
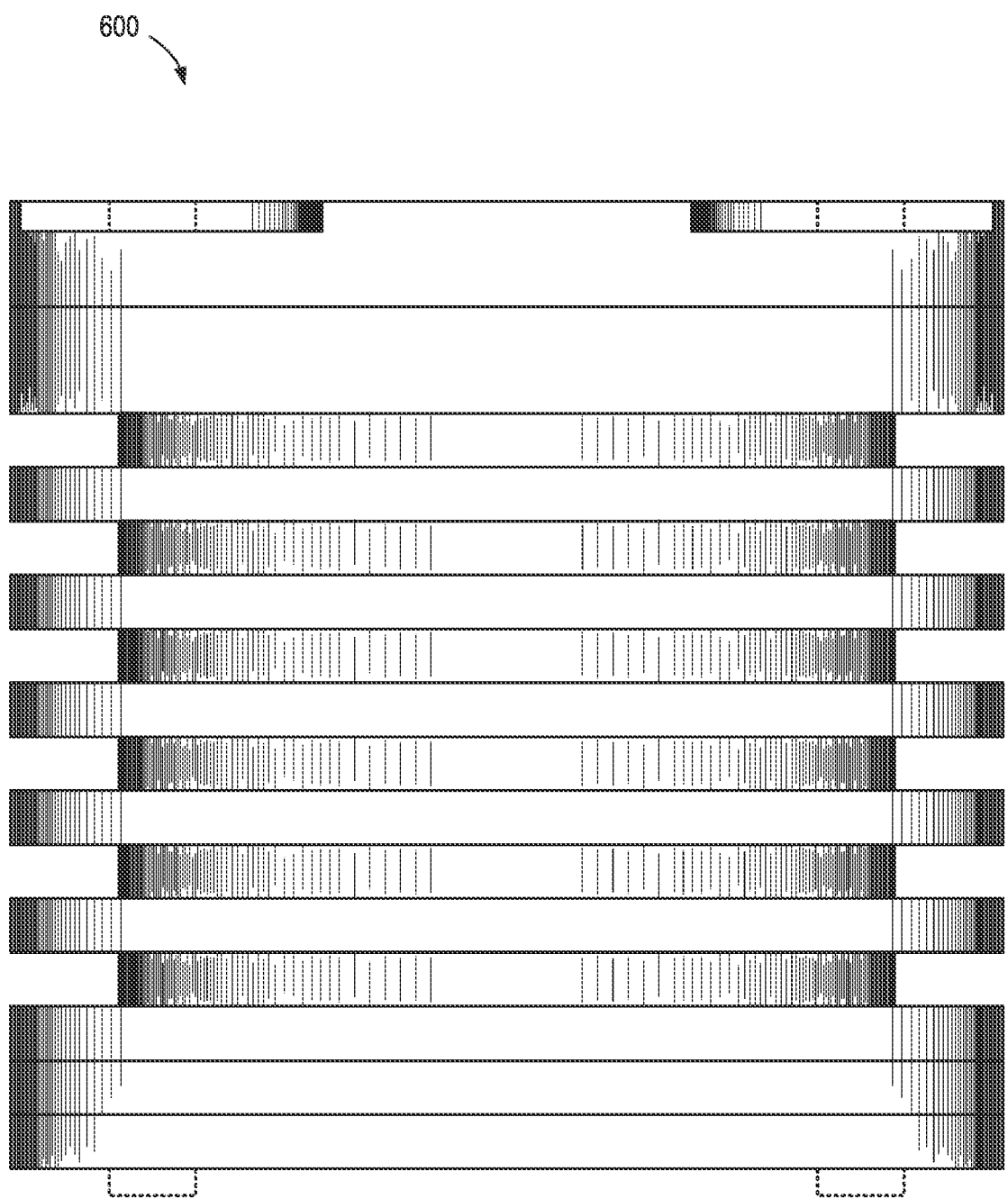
FIG. 6F is a rear-side elevation view of the UVC light housing of FIG. 6A, according to one embodiment.

FIG. 6F is a rear-side elevation view of the UVC light housing of FIG. 6A, according to one embodiment.

Figure 6G:
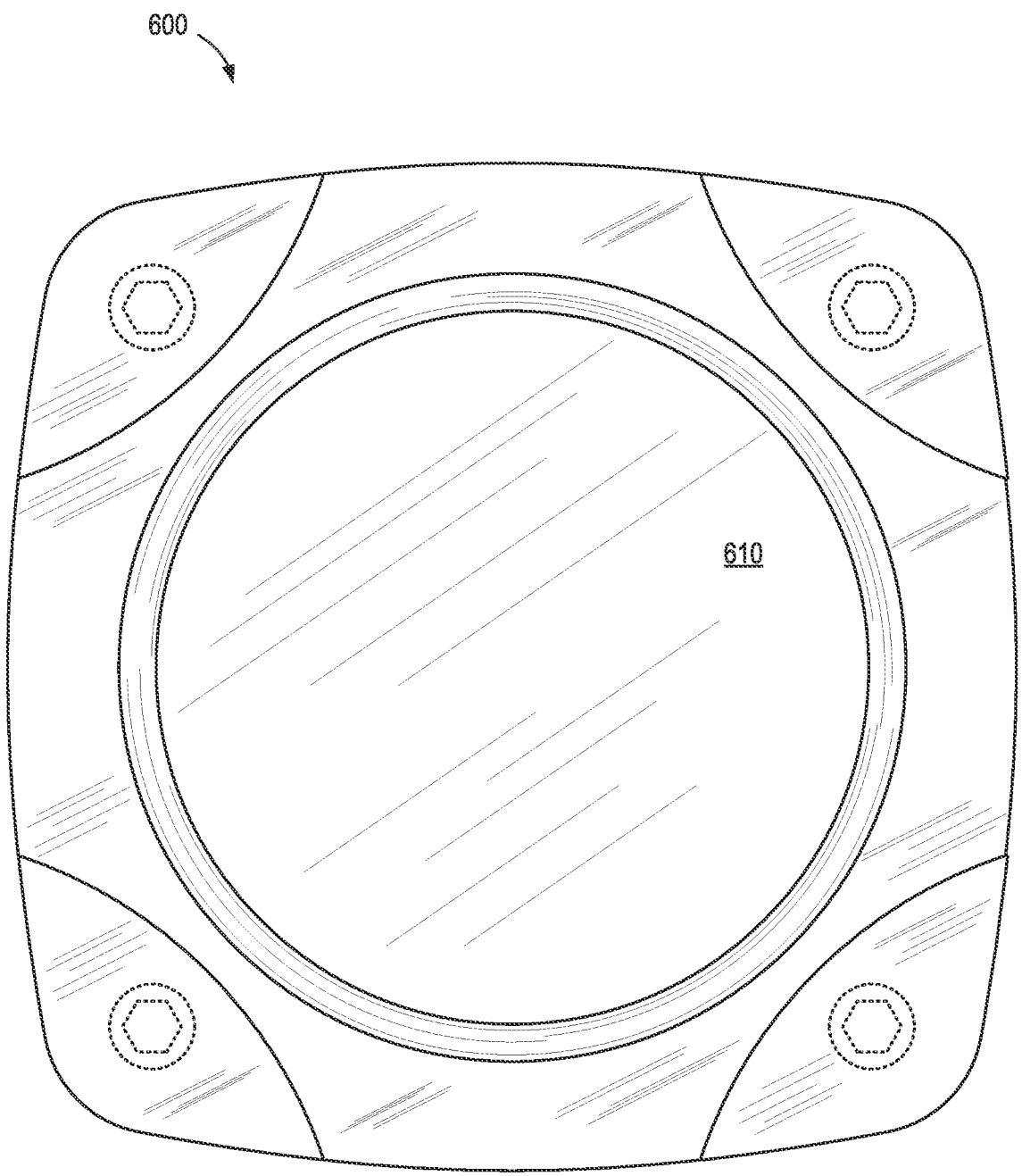
FIG. 6G is a top plan view of the UVC light housing of FIG. 6A, according to one embodiment.

FIG. 6G is a top plan view of the UVC light housing of FIG. 6A, according to one embodiment.

Figure 6H:
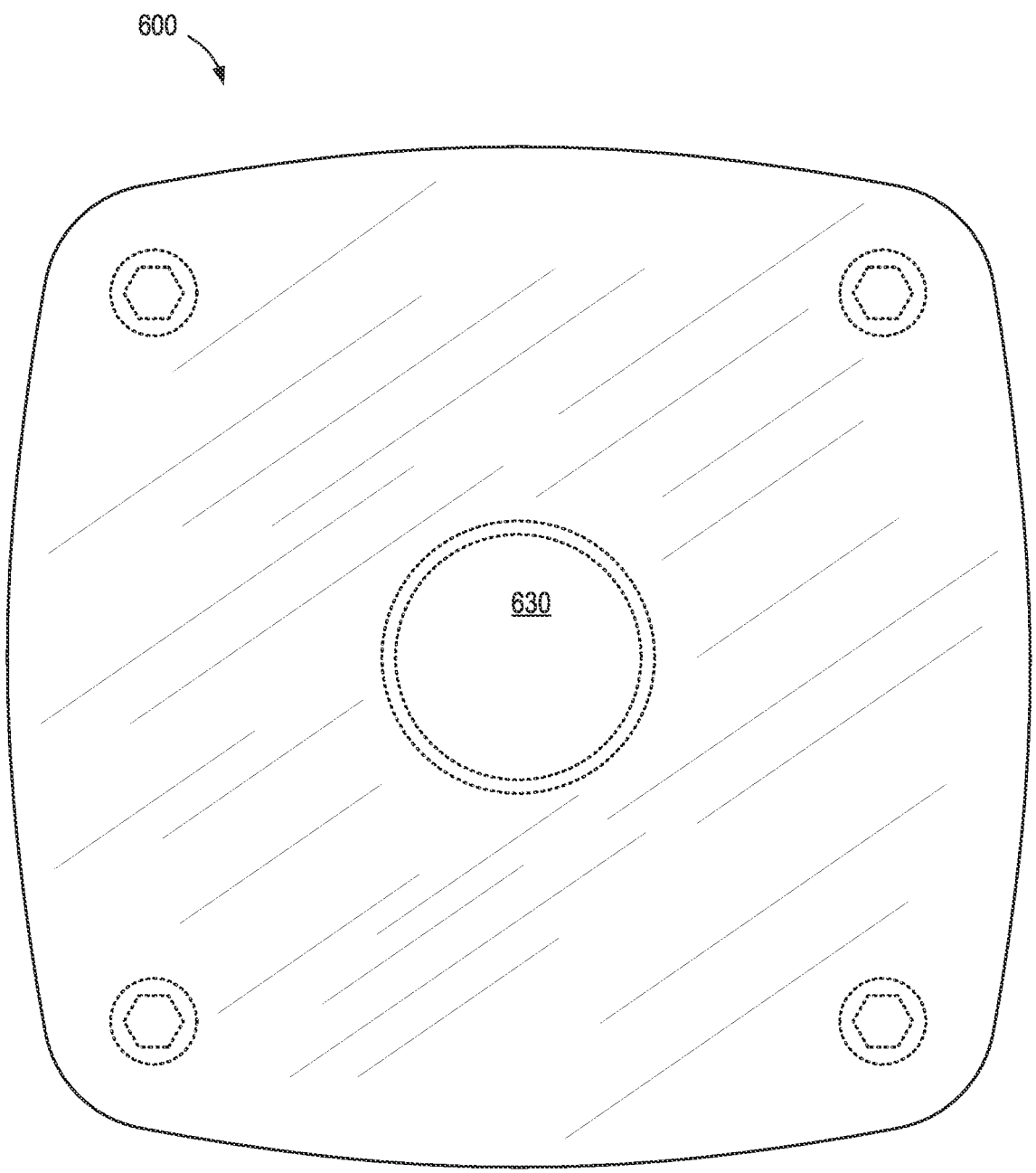
FIG. 6H is a bottom plan view of the UVC light housing of FIG. 6A, according to one embodiment.

FIG. 6H is a bottom plan view of the UVC light housing of FIG. 6A, according to one embodiment.

The various embodiments of systems and methods described herein improve the flexibility of LED lights in various industrial and residential applications. The above description provides numerous specific details for a thorough understanding of the embodiments described herein; however, one or more of the specific details may be omitted, modified, and/or replaced by a similar process or system. The scope of this disclosure should be interpreted as encompassing the claims set forth below, which are included as part of this specification.

What is claimed:

1. An ultraviolet sterilization system, comprising:
   an ultraviolet light assembly, comprising:
      a housing;
      a heatsink element connected to the housing;
      an array of ultraviolet light-emitting diodes (LEDs) housed within the housing to generate a directional beam of ultraviolet radiation;
      an electronic driver housed within the housing to drive the ultraviolet LEDs; and
      a power interface to receive power from an external power source;
   a duct mounting interface configured to be secured proximate a hole in an air duct and to selectively mount and releasably unmount the ultraviolet light assembly from the air duct, such that with the ultraviolet light assembly mounted to the air duct via the duct mounting interface, the directional beam of ultraviolet radiation operates to sterilize air passing through the air duct;
   a first power supply comprising at least a power cord to connect the power interface of the ultraviolet light assembly to an alternating current (AC) power receptacle with the ultraviolet light assembly mounted to the air duct; and
   a second power supply comprising a portable DC power source and a power cord to connect the power interface of the ultraviolet light assembly to the DC power source,
   wherein the ultraviolet light assembly is configured to be selectively unmounted from the duct mounting interface and used in a handheld configuration to selectively sterilize a surface within a region illuminated by the directional beam of ultraviolet radiation.

2. The system of claim 1, wherein the ultraviolet light assembly further comprises a user-adjustable focusing lens to focus a spot size of the directional beam of ultraviolet radiation.

3. The system of claim 1, wherein the ultraviolet LEDs are configured to generate ultraviolet C (UVC) optical radiation.

4. The system of claim 1, wherein the ultraviolet light assembly further comprises an elongated handle that can be selectively bent and repositioned by a user to maintain a target shape during portable use.

5. The system of claim 1, wherein the ultraviolet light assembly further comprises at least one internal power source housed within the housing.

6. The system of claim 5, wherein the at least one internal power source comprises one or more of: a rechargeable battery, a capacitor, and a single-use disposable battery.

7. The system of claim 1, wherein the heatsink element connected to the housing forms at least a portion of an outer surface of the housing.

8. The system of claim 1, further comprising:
a wall mounting interface configured to be permanently secured to a wall and to selectively secure and release the ultraviolet light assembly from a wall-mounted position.

9. The system of claim 1, further comprising:
a desktop mounting stand configured to be placed on a planar surface and to selectively secure and release the ultraviolet light assembly from a desktop-mounted position.

10. The system of claim 1, further comprising:
a portable large surface cleaning mount configured to selectively secure and release multiple ultraviolet light assemblies for mobile sterilization of large surfaces, wherein the portable large surface cleaning mount has an integrated power supply and power cords to connect multiple ultraviolet light assemblies.

11. An ultraviolet light assembly, comprising:
a housing;
a heatsink element connected to the housing;
an array of ultraviolet light-emitting diodes (LEDs) housed within the housing to generate a directional beam of ultraviolet radiation;
an electronic driver housed within the housing to drive the ultraviolet LEDs; and
a power supply system configured for dynamic operation in:
a first operational configuration in which the ultraviolet light assembly is configured for stationary sterilization while connected to an alternating current (AC) power source, and
a second operational configuration in which the ultraviolet light assembly is configured for mobile sterilization while connected to a portable direct current (DC) power source,
wherein the ultraviolet light assembly is configured to be selectively retained by a duct mounting system for operation in the first operational configuration with the directional beam of ultraviolet radiation directed into an air duct for sterilization of air within the air duct.

12. The assembly of claim 11, wherein the ultraviolet light assembly is configured to be selectively operated in a portable handheld mode in the second operational configuration in which a user can selectively direct the directional beam of ultraviolet radiation onto a surface for selective sterilization.

13. The assembly of claim 12, wherein the ultraviolet light assembly further comprises an integrated handle to facilitate operation in the portable handheld mode.

14. The assembly of claim 12, wherein the ultraviolet light assembly further comprises an integrated battery to provide the portable DC power source in the second operational configuration during use in the portable handheld mode.

15. The assembly of claim 12, further comprising:
a detachable handle that can be selectively connected to the housing of the ultraviolet light assembly during operation in the handheld mode.

16. The assembly of claim 15, wherein the detachable handle comprises an integrated DC power source.

17. The assembly of claim 12, further comprising:
a flexible cord that can be used as a handle that can be repositioned and bent into different positions, wherein the flexible cord maintains its shape in said repositioned and bent positions.

18. An ultraviolet light assembly, comprising:
a housing;
a heatsink element connected to the housing;
an array of ultraviolet light-emitting diodes (LEDs) housed within the housing to generate a directional beam of ultraviolet radiation;
an electronic driver housed within the housing to drive the ultraviolet LEDs; and
a reconfigurable handle that can be selectively repositioned by a user in fixed positions to facilitate aiming the directional beam of ultraviolet radiation onto a surface for sterilization of said surface,
wherein the ultraviolet light assembly is configured to be selectively retained by a duct mounting system such that the directional beam of ultraviolet radiation is directed into an air duct for sterilization of air within the air duct.

19. The ultraviolet light assembly of claim 18, further comprising:
a portable battery back that can be plugged into the ultraviolet light assembly during handheld operation.

* * * * *